United States Patent [19]

Kume et al.

[11] Patent Number: 4,798,620

[45] Date of Patent: Jan. 17, 1989

[54] BENZOXAZINES AND HERBICIDAL USE

[75] Inventors: Toyohiko Kume; Toshio Goto; Atsumi Kamochi; Shigeki Yagi, all of Tokyo, Japan

[73] Assignee: Nihon Tokushu Noyaku Seizo K.K., Tokyo, Japan

[21] Appl. No.: 187,713

[22] Filed: Apr. 29, 1988

Related U.S. Application Data

[63] Continuation-in-part of Ser. No. 88,921, Aug. 24, 1987.

[30] Foreign Application Priority Data

Sep. 6, 1986 [JP] Japan ................................. 61-210725
May 9, 1987 [JP] Japan ................................. 62-111696
Oct. 2, 1987 [JP] Japan ................................. 62-27194
Feb. 2, 1988 [JP] Japan ................................. 63-21359

[51] Int. Cl.[4] ..................... A01N 43/84; C07D 413/04
[52] U.S. Cl. ............................................. 71/95; 71/96; 544/105
[58] Field of Search ....................... 544/105; 71/95, 96

[56] References Cited

U.S. PATENT DOCUMENTS 4,640,707 2/1987 Nagano et al. ................. 544/105 X
4,729,784 3/1988 Kume et al. ................... 544/105 X Primary Examiner—Richard L. Raymond
Attorney, Agent, or Firm—Sprung Horn Kramer & Woods

[57] ABSTRACT

Novel benzoxazines of the formulae (I), (III), (IV), (V), (VII) and (XIV).

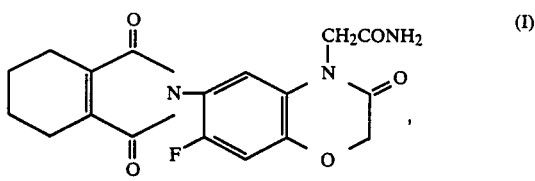

(I)

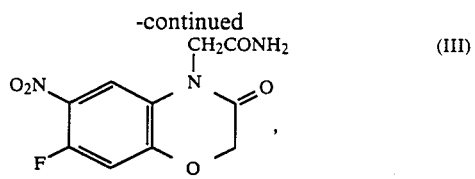

(III)

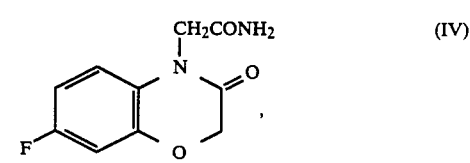

(IV)

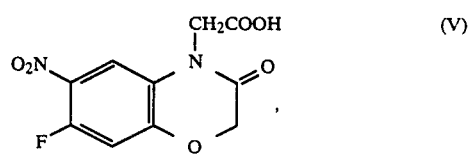

(V)

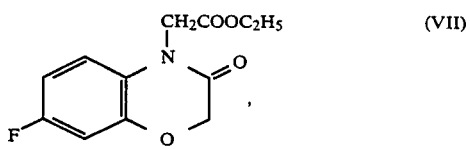

(VII)

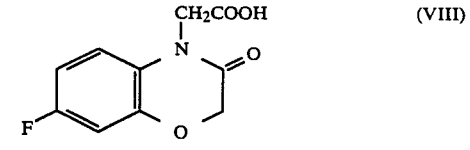

(VIII)

and

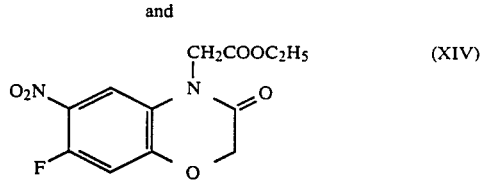
(XIV)

Compound I is herbicidal and can also be reacted to convert the aminocarbonyl group to a nitrile, the resulting product also being herbicidal.

3 Claims, No Drawings

BENZOXAZINES AND HERBICIDAL USE

This is a continuation-in-part of application Ser. No. 088,921, filed Aug. 24, 1987, now pending.

The present invention relates to novel benzoxazines, to processes for their preparation and to their use as intermediates.

There has now been found novel 2-[4-carbamoyl-methyl-7-fluoro-2H-1,4-benzoxazin-3(4H)on-6-yl]4,5,6,7-tetrahydro-2H-isoindole-1,3-dione of the formula (I)

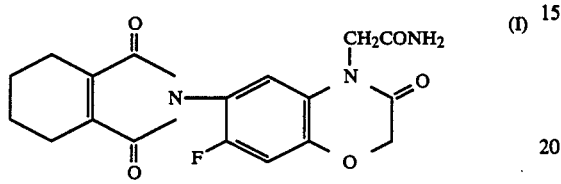

The compound of the formula (I) is obtained by a process in which (a) 4-carbamoylmethyl-7-fluoro-6-amino-2H-1,4-benzoxazin-3(4H)-one of the formula (II)

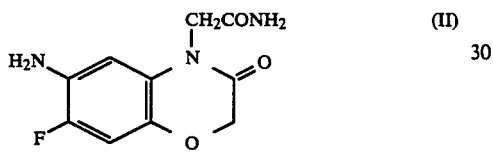

is reacted with 3,4,5,6-tetrahydrophthalic anhydride, in the presence of inert solvents.

As shown in the hereinafter described Referential Examples, the benzoxazine of the formula (I) according to the present invention is useful as a novel intermediate for the preparation of herbicidally active 2-[4-cyanomethyl-7-fluoro-2H-1,4-benzoxazin-3(4)on-6-yl]-4,5,6,7-tetrahydro-2H-isoindole-1,3-dione represented by the following formula:

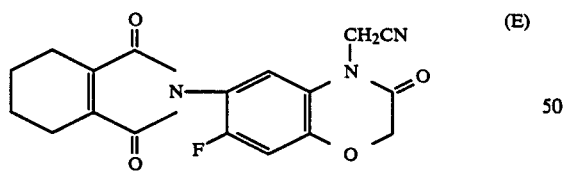

Prepared by a different process in parent application Ser. No. 088,921, supra, the disclosure of which is incorporated herein by reference.

The process (a) can be represented by the following equation:

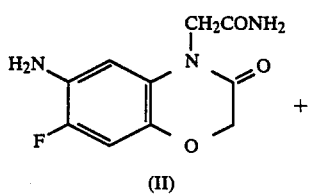

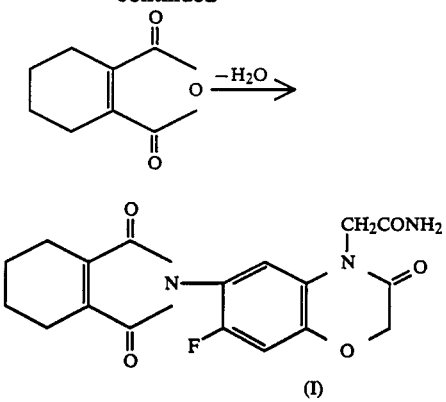

As shown in the hereinafter described examples, the compound of the formula (II) in process (a) can be prepared by a process in which (b) 4-carbamoylmethyl-7-fluoro-6-nitro-2H-1,4-benzoxazin-3(4)-one of the formula (III)

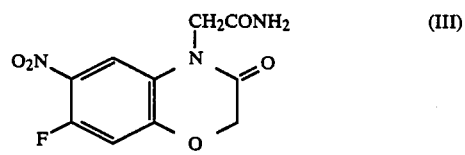

is reduced, in the presence of inert solvents and in the presence of a catalytic amount of palladium-carbon.

In the process (b), a, catalytic reduction by using a catalytic amount of palladium-carbon easily and simply takes place.

Furthermore, a conventional reduction method is also applicable by using iron in the presence of an acid such as acetic acid.

The compound of the above formula (III) in the process (b) is a novel compound, and it can be prepared, as shown in the hereinafter described examples, by a process in which (c) 4-carbamoylmethyl-7-fluoro-2H-1,4-benzoxazin-3(4H)-one of the formula (IV)

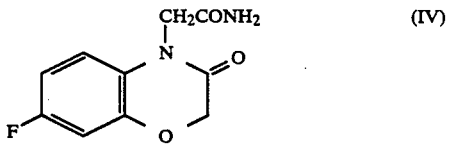

is reacted with concentrated nitric acid in the presence of sulfuric acid, or (d) 4-carboxymethyl-7-fluoro-6-nitro-2H-1,4-benzoxazin-3(4H)-one represented by the formula (V)

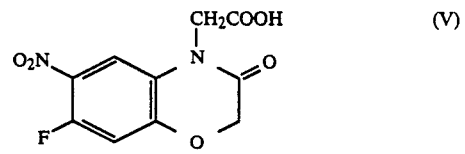

is reacted with thionyl chloride in the presence of inert solvents, and the resulting product is further reacted with ammonia.

The process (c) can be conducted according to the nitration reaction described in "Synthetic Organic Chemistry", pp. 747-749, or in the specification of EP-OS No. 170,191.

The process (d) can be conducted according to hereinafter stated process (g) and process (e).

The compound of the above formula (IV) in the process (c) is a novel compound, and it can be prepared, for example, by a process in which (e) 4-chlorocarbonylmethyl-7-fluoro-2H-1,4-benzoxazin-3(4H)-one of the formula (VI)

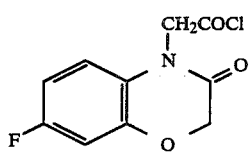

is reacted with ammonia in the presence of inert solvents, (f) 4-ethoxycarbonylmethyl-7-fluoro-2H-1,4-benzoxazin-3(4H)-one represented by the formula (VII)

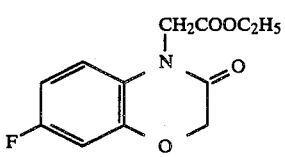

is reacted with ammonia in the presence of inert solvents.

The compound of the formula (VI) in the process (e) is a novel compound, and can be prepared, as shown in the hereinafter described examples, by a process in which (g) 4-carboxymethyl-7-fluoro-2H-1,4-benzoxazin-3(4H)-one of the formula,

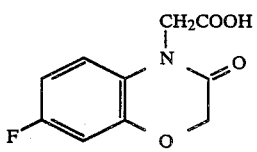

is reacted with thionyl chloride in the presence of inert solvents.

In carrying out the above process (g) and then process (e) for synthesizing the compound of the formula (IV) in the above process (c), the compound of the formula (IV) can be prepared readily by reacting the compound of the formula (VIII) with thionyl chloride, and subsequently reacting the resulting product with ammonia, instead of separating the compound of the formula (VI), as shown by example hereinbelow.

The process (f) can be conducted according to the description of Synthetic Organic Chemistry, pp. 565-569, R. B. Wagner, H. D. Zook, issued in 1953 by John Wiley & Sons Inc.

The compound of the above formula (VIII) in the process (g) is a novel compound, and can be prepared, as shown by example hereinbelow, by a process in which (h) 4-ethoxycarbonylmethyl-7-fluoro-2H-1,4-benzoxazin-3(4H)-one of the above formula (VII) is hydrolyzed in the presence of inert solvents.

The compound of the formula (VII) in the process (f) and the process (h) can be prepared, as shown by example hereinbelow, by a process in which (i) 7-[4-(ethoxycarbonylmethyl)-2H-1,4-benzoxazin-3(4H)-one]diazoniumtetrafluoroborate of the formula (IX)

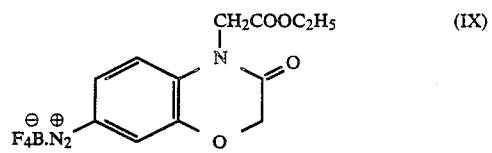

is thermally decomposed in the presence of inert solvents.

The process (i) can be conducted, according to the Schiemann Reaction described in Organic Reactions, No. 5, pp. 199-206.

The compound of the above formula (IX) in the process (i) can be prepared, as shown by example hereinbelow, by a process in which (j) 7-amino-4-ethoxycarbonylmethyl-2H-1,4-benzoxazin-3(4H)-one of the formula (X)

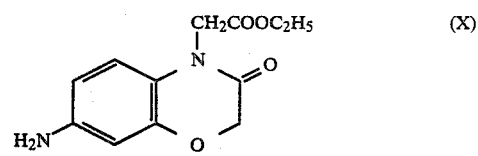

is reacted with sodium nitrite and tetrafluoroboric acid in the presence of inert solvents.

The compound of the above formula (X) in the process (j) can be prepared readily, as shown in the referential example hereinbelow, by a process in which (k) 4-ethoxycarbonylmethyl-7-nitro-2H-1,4-benzoxazin-3(4H)-one of the formula (XI)

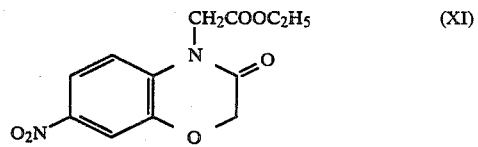

is reduced in the presence of inert solvents.

The compound of the above formula (XI) can be prepared readily, as shown by example hereinbelow, by a process in which (l) 7-nitro-2H-1,4-benzoxazin-3(4H)-one of the formula (XII)

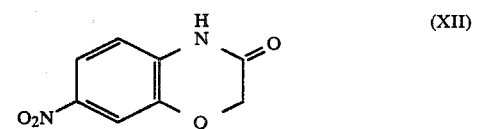

is reacted with the ethyl ester of an α-halogenoaceticacid, preferably with ethyl bromoacetate, or (m) 2-amino-5-nitrophenol of the formula (XIII)

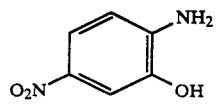 (XIII)

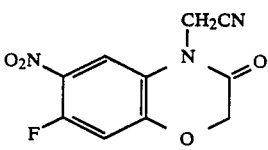 (XVI)

is reacted with ethyl bromoacetate.

The above process (l) can be conducted according to the process described in "Yakugaku Zasshi (Pharmacological Journal)" Vol. 86 (No. 3), 1966, pp. 209–213.

The process (m) can be conducted by reacting two equivalents of ethyl bromoacetate per equivalent of the compound of the formula (XIII) in the presence of an excess of a base, for example, potassium carbonate.

The compound of the formula (XII) in the process (l) can be prepared from 2-amino-5-nitrophenol, as described in "Synthesis", 1982, pp. 986–987.

The compound of the formula (V) in the process (d) is a novel compound, and can be prepared, as shown in the example hereinbelow, by a process in which (n) 4-ethoxycarbonyl-7-fluoro-6-nitro-2H-1,4-benzoxazin-3(4H)-one of the formula (XIV)

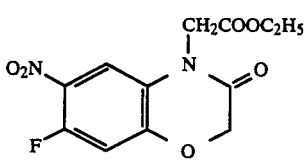 (XIV)

is hydrolyzed in the presence of inert solvents, or (o) 4-carboxymethyl-7-fluoro-2H-1,4-benzoxazin-3(4H)-one of the formula (VIII) is reacted with concentrated nitric acid in the presence of sulfuric acid.

The compound of the formula (XIV) in process (n) is a novel compound, and can be prepared by a process in which (p) 4-ethoxycarbonylmlethyl-7-fluoro-2H-1,4-benzoxazin-3(4H)-one of the formula (VII) is reacted with concentrated nitric acid in the presence of sulfuric acid.

On the other hand, 4-carbamoylmethyl-7-fluoro-6-nitro-2H-1,4-benzoxazin-3(4H)-one of the formula (III), and 4-carbamoylmlethyl-7-fluoro-6-nitro-2H-1,4-benzoxazin-3(4H)-one of the formula (IV) are respectively intermediates in an alternative process for the preparation of the herbicidal compound of the formula (E) hereinabove.

That is, as shown as alternative process in the referential example hereinbelow, the herbicidal compound of the formula (E) can be prepared by reacting 6-amino-4-cyanomethyl-7-fluoro-2H-1,4-benzoxazin-3(4H)-one of the formula (XV)

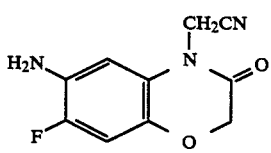 (XV)

with tetrahydrophthalic anhydride.

The compound of the formula (XV) is an unknown novel compound, and it can be prepared by a process in which (q) 4-cyanomethyl-7-fluoro-6-nitro-2H-1,4-benzoxazin-3(4H)-one of the formula (XVI)

is reduced in the presence of inert solvents.

The process (q) can be conducted using iron and acetic acid, described in "Berichte", Vol. 17, p. 343.

The compound of the formula (XVI) in the process (q) is a novel compound, and as shown by example hereinbelow, can be prepared by a process in which (r) 4-carbamoylmethyl-7-fluoro-6-nitro-2H-1,4-benzoxazin-3(4H)-one of the formula (III) is reacted with thionyl chloride in the presence of a catalytic amount of N,N-dimethylformamide or (s) 4-cyanomethyl-7-fluoro-2H-1,4-benzoxazin-3(4H)-one of the formula (XVII)

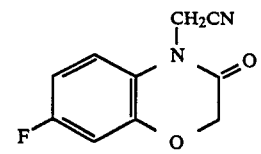 (XVII)

is reacted with concentrated nitric acid and acetic anhydride in the presence of a catalytic amount of sulfuric acid.

The compound of the formula (XVII) in the process (s) is a novel compound, and as shown by example hereinbelow, it can be prepared by a process in which (t) 4-carbamoylmethyl-7-fluoro-2H-1,4-benzoxazin-3(4H)-one of the formula (IV) is reacted with thionyl chloride in the presence of a catalytic amount of N,N-dimethylformamide.

A conversion of the amide derivative compound into the nitrile (cyano derivative compound) by dehydration, in the process (r) and process (t), can be carried out according to the description in The Chemistry of IMIDOYL HALIDES by H. Ulrich, Lenum Press, New York, (pp. 55–105).

In conducting the process (a), organic acids such as acetic acid or propionic acid and the like may be used as a diluent, and the process can be conducted at a temperature from room temperature to the boiling point of the organic acid used.

It is preferred to carry out the reaction under normal pressures, although a higher or lower pressure can also be used.

In conducting the process (a), for example, about 1 to 1.2 moles of tetrahydrophthalic anhydride per mole of the compound of the formula (II) are reacted with each other in the presence of the above diluent to give the desired compound of the formula (I).

In conducting the process (b), as appropriate diluents, all kinds of inert organic solvents can be mentioned.

Examples of the diluents are water; aliphatic, alicyclic, and aromatic hydrocarbons (they may be chlorinated, according to circumstances), such as hexane, cyclohexane, petroleum ether, ligroin, benzene, toluene, xylene, methylene chloride, chloroform, carbon tetrachloride, ethylene chloride, chlorobenzene; and further ethers, such as diethyl ether, methyl ethyl ether, di-isopropyl ether, dibutyl ether, dioxane, tetrahydrofuran; alcohols, such as methanol, ethanol, isopropanol;

esters, such as ethyl acetate, amyl acetate; acid amides, such as dimethylformamide, dimethylacetamide; sulfones and sulfoxides, such as dimethyl sulfoxide, sulfolane; and organic acids, such as acetic acid and the like.

The process (b) can be conducted substantially in a wide range of temperature. Generally it can be carried out at a temperature of about 0° C. to about 150° C., preferably about 20° C. to about 100° C. It is preferred to carry out the reaction under normal pressure, although a higher or lower pressure can also be used.

In conducting the processes (c), (o) and (p), as appropriate diluents there can be mentioned sulfuric acid, acetic acid or acetic anhydride, and the like. It can be carried out generally at a temperature of about −20° C. to about 30° C., preferably about 0° C. to about 20° c.

In conducting the processes (d), (e) and (g), every kind of inert organic solvent can be mentioned as appropriate diluent.

Examples of the diluents are water; aliphatic, alicyclic and aromatic hydrocarbons (they may be chlorinated, according to circumstances), such as hexane, cyclohexane, petroleum ether, ligroin, benzene, toluene, xylene, methylene chloride, chloroform, carbon tetrachloride, ethylene chloride, chlorobenzene; and further ethers, such as diethyl ether, methyl ethyl ether, di-isopropyl ether, dibutyl ether, dioxane, tetrahydrofuran; ketones, such as acetone, methyl ethyl ketone, methyl isopropyl ketone, methyl isobutyl ketone; nitriles, such as acetonitrile, propionitrile, acrylonitrile; alcohols, such as methanol; esters, such as ethyl acetate, amyl acetate; acid amides, such as dimethylformamide, dimethylacetoamide; sulfones and sulfoxides, such as dimethyl sulfoxide, sulfolane; and bases, such as pyridine, and the like.

The processes (d), (e) and (g) can be conducted substantially over a wide range of temperature. They can be carried out generally at a temperature of about −20° C. to about 150° C., preferably about 0° C. to about 100° C. The reaction is preferably carried out under normal pressure, although a higher or lower pressure can also be used.

In conducting the process (f), every kind of inert organic solvent can be mentioned as appropriate diluent.

Examples of the diluents are water; aliphatic, alicyclic and aromatic hydrocarbons (they may be chlorinated according to circumstances), such as hexane, cyclohexane, petroleum ether, ligroin, benzene, toluene, xylene, chlorobenzene; and further ethers, such as diethyl ether, methyl ethyl ether, di-isopropyl ether, dibutyl ether, dioxane, tetrahydrofuran; ketones, such as acetone, methyl ethyl ketone, methyl-isopropyl ketone, methyl-isobutyl ketone; alcohols, such as methanol, ethanol, isopropanol, butanol, ethylene glycol, and the like.

The process (f) can be conducted substantially over a wide range of temperature. It can be carried out generally at a temperature of about 50° C. to 200° C., preferably about 80° C. to about 150° C. The reaction can be carried out under normal pressure, although a higher or lower pressure can also be used.

In conducting the processes (h) and (n), every kind of inert organic solvent can be mentioned as appropriate diluent Examples of the diluents are water; aliphatic, alicyclic and aromatic hydrocarbons (they may be chlorinated, according to circumstances), such as hexane, cyclohexane, petroleum ether, ligroin, benzene, toluene, xylene, methylene chloride, chloroform, carbon tetrachloride, ethylene chloride, chlorobenzene; and further ethers, such as diethyl ether, methyl ethyl ether, di-isopropyl ether, dibutyl ether, dioxane, tetrahydrofuran; ketones, such as acetone, methyl ethyl ketone, methyl isopropyl ketone, methyl isobutyl ketone; nitriles, such as acetonitrile, propionitrile, acrylonitrile; alcohols, such as methanol, ethanol, isopropanol, butanol, ethylene glycol; acid amides, such as dimethylformamide, dimethylacetoamide; sulfones and sulfoxides, such as dimethyl sulfoxide, sulfolane; and bases, such as piridine, and the like.

The processes (h) and (n) can be conducted substantially over a wide range of temperature. They can be carried out generally at a temperature of about −20° C. to about 150° C., preferably about −10° C. to about 100° C. It is preferred to carry out the reaction under normal pressure, although a higher or lower pressure can also be used.

In conducting the process (i), as appropriate diluents there can be mentioned every kind of inert organic solvent having a boiling point of at least the thermal decomposition point (about 130° C.) of the compound of formula (IX).

Examples of such diluents are aliphatic, alicyclic and aromatic hydrocarbons (they may be chlorinated, according to circumstances), such as petroleum ether, xylene, chlorobenzene, and the like.

The process (i) can be conducted substantially over a wide range of temperatures. It can be carried out generally at a temperature of about 125° C. to about 180° C., preferably about 130° C. to about 140° C. It is preferred to carry out the reaction under normal pressure, although a higher or lower pressure can also be used.

In conducting the process (j), as appropriate diluents there can be mentioned water, dilute hydrochloric acid, concentrated hydrochloric acid, borofluoric acid and the like.

The process (j) can be conducted substantially over a range of temperatures. It can be carried out generally at a temperature of about −30° C. to about 30° C., preferably about −20° C. to about 20° C. It is referred to carry out the reaction under normal pressure, although a higher and lower pressure can also be used.

In conducting the process (q), as appropriate diluents there can be mentioned water; alcohols, such as methanol, ethanol, isopropanol, butanol, ethylene glycol; esters, such as ethyl acetate, amyl acetate; and organic acids, such as acetic acid, and the like.

The process (q) can be conducted substantially over a wide range of temperatures. It may be carried out generally at a temperature of about 0° C. to about 120° C., preferably about 30° C. to about 90° C. It is preferred to carry out the reaction under normal pressure, although a higher or lower pressure can also be used.

In conducting the processes (r) and (t), as appropriate diluents there can be mentioned every kind of inert organic solvent.

As examples of such diluents there can be mentioned aliphatic, alicyclic and aromatic hydrocarbons (they may be chlorinated according to circumstances), such as hexane, cyclohexane, petroleum ether, ligroin, benzene, toluene, xylene, methylene chloride, chlorobenzene; and further, ethers, such as di-isopropyl ether, dibutyl ether, dioxane; nitriles, such as acetonitrile, propionitrile; esters, such as ethyl acetate, amyl acetate; acid amides, such as dimethylformamide, dimlethylacetamide; sulfones and sulfoxides, such as dimethyl sulfoxide, sulfolane; and bases, such as pyridine, and the like.

The processes (r) and (t) may be conducted substantially over a wide range of temperature. They can be carried out generally at a temperature of about 60° C. to about 200° C., preferably about 80° C. to about 150° C. It is preferred to carry out the reaction under normal pressure, although a higher or lower pressure can also be used.

In conducting the process (s), as appropriate diluents there can be mentioned every kind of inert organic solvent.

As examples of such diluents there can be mentioned aliphatic, alicyclic and aromatic hydrocarbons (they may be chlorinated, according to circumstances), such as hexane, cyclohexane, petroleum ether, ligroin, methylene chloride, chloroform, carbon tetrachloride, ethylene chloride, chlorobenzene nitrobenzene; and further ethers, such as diethyl ether, methyl ethyl ether, di-isopropyl ether, dibutyl ether, dioxane, tetrahydrofuran; and organic acids, such as acetic acid, propionic acid, and the like.

The process (s) may be conducted substantially over a wide range of temperature. It may be carried out generally at a temperature of about −20° C. to about 30° C., preferably about −10° C. to about 20° C. It is preferred to carry out the reaction under normal pressure, although a higher or lower pressure can also be used.

IN conducting the process (s), hydrolysis of the cyano group will occur very rapidly due to the action of frequently used mixed acids, but such problem can be solved by using acetyl nitrate.

Further the amino derivative compound of the formula (XX)

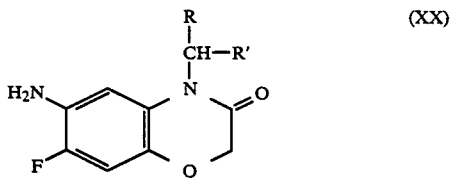

where R represents a hydrogen atom or methyl, R' represents an alkyl, alkylthioalkyl, cycloalkyl, or aromatic heterocyclic group such as pyridyl, etc, can be prepared by the following process, wherein as a starting material, the compound of the formula (XII), 7-nitro-2H-1,4-benzoxazin-3(4H)-one of the formula (XII) is reacted with the compound which is known generally as an alkylating agent and represented by the formula (XVIII)

in which, Z represents halogen, or —OSO₂—R″ wherein R″ represents alkyl, or aryl which may optionally have a substituent; R and R' are the same as above, subsequently the resulting product is subjected to reduction according to the process (k), and through the same procedures as employed in the processes (j) and (i), further subjected to either the process (c) or the process (s) to produce a nitro derivative compound of the formula (XIX)

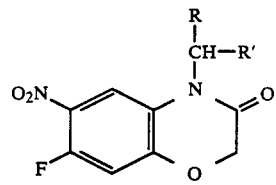

in which R and R' are respectively the same as above, and the resulting compound of the formula (XIX) is reduced by a conventional reduction reaction, for example, according to the process (b) or the process (q).

The concept of the present invention will be explained concretely hereinbelow according to the embodiments of the invention and referential examples, but it should be noted that the scope of the invention should not be limited only to the technical contents of the examples.

EXAMPLES OF SYNTHESIS

Example 1

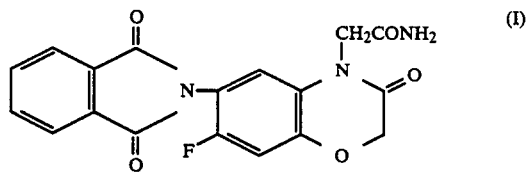

A mixture of 4-carbamoylmethyl-7-fluoro-6-nitro-2H-1,4-benzoxazin-3(4H)-one (1.78 g), N,N-dimethylformamide (50 ml), and 10% palladiumcarbon (0.3 g) was catalytically reduced under normal pressure. When absorption of hydrogen gas terminated, the resulting product was filtered, subsequently the solvent was distilled off under a reduced pressure, then acetic acid (30 ml) and tetrahydrophthalic anhydride (1 g) were added to the residue, and the mixture was refluxed for 3 hours under heating. After the reaction terminated, the solvent was distilled off under reduced pressure, and tetrahydrofuran (100 ml) was added to the residue, the liquor was filtered while hot, and the filtrate was distilled under a reduced pressure to obtain a residue solid. The residue solid was washed with toluene, then ethanol (150 ml) and activated carbon (0.5 g) were added thereto, and heated for one minute, and filtered. The filtrate was concentrated, and cooled to room temperature, then filtered off. The obtained product was washed with n-hexane to give the desired 2-[4-carbamoylmethyl-7-fluoro-2H-1,4-benzoxazin-3(4H)-on-6-yl]-4,5,6,7-tetrahydro-2H-isoindole-1,3-dione (0.5 g). mp. 283°–286° C.

Example 2

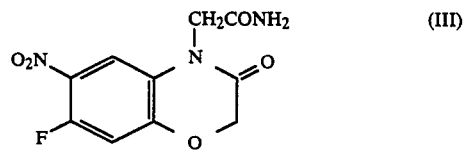

4-carbamoylmllethyl-7-fluoro-2H-1,4-benzoxazin-3(4H)-one (4.48 g) was cooled to a temperature of 0° C. to 5° C., then it was added to concentrated sulfuric acid, and the mixture was fully stirred. 98% Nitric acid (1,42 g) was added dropwise thereto at a temperature of 0° C. to 5° C. After the liquor was stirred for an hour, it was poured into ice-cold water, then the produced solid was filtered off, and washed with water, then dried to give the desired 4-carbamoylmethyl-7-fluoro-6-nitro-2H-1,4-benzoxazin-3(4H)-one (4.0 g). mp. 220°–226° C.

Example 3

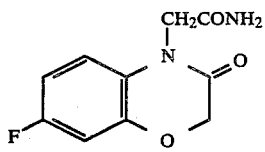

Three drops of pyridine were added to a mixture of 4-carboxymethyl-7-fluoro-2H-1,4-benzoxazin-3(4H)-one (2.25 g), chloroform (18 g) and thionylchloride (3.6 g), then the mixture was refluxed under heating for 5 hours. After the solvent was concentrated, it was mixed with toluene (50 ml), after the solvent was distilled off, the residue was dissolved in toluene (60 ml), and ammonia gas was introduced into the solution at a temperature of 10° C. to 20° C. After ammonia was saturated, the solution was stirred at room temperature for an hour, and the solid was filtered off, and then washed with toluene, sodium bicarbonate solution, and water in that order, and dried to give the desired 4-carbamoylmethyl-7-fluoro-2H-1,4-benzoxazin-3(4H)-one (2.1 g). mp. 212°–214° C.

Example 4

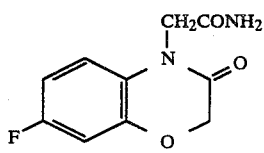

A mixture of 4-ethoxycarbonylmethyl-7-fluoro-2H-1,4-benzoxazin-3(4H)-one (1.27 g), ethanol (20 ml) and 28% ammonia water (10 g) was mixed at room temperature for 2 hours, and refluxed for 3 hours. After the solvent was concentrated, it was mixed with water, and filtered. Resulting product was washed with water and ethanol in that order, and recrystallized from methylisobutyl ketone to give the desired 4-carbamoylmethyl-7-fluoro-2H-1,4-benzoxazin-3(4H)-one (0.45 g). mp. 216.5°–219° C.

Example 5

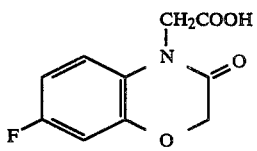

Sodium hydroxide (0.7 g) and water (10 ml) were added to a mixture of 4-ethoxycarbonylmethyl-7-fluoro-2H-1,4-benzoxazin-3(4H)-one (3.7 g) and ethanol (20 ml), and the mixture was refluxed under heating for 5 hours. After the reaction, the solvent was concentrated, and dissolved in water (50 ml), and washed with methylisobutyl ketone, the aqueous layer was acidified with hydrochloric acid, and extracted with methyl isobutyl ketone, then dried with anhydrous sodium sulfate. After the solvent was distilled off, the residue was mixed with a mixed solvent of toluene-hexane (1:5), the mixture was filtered off to give the desired 4-carboxymethyl-7-fluoro-2H-1,4-benzoxazin-3(4H)-one (3.2 g). mp. 183°–184° C.

Example 6

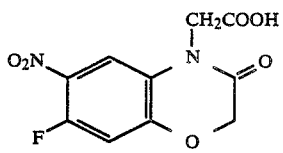

Sodium hydroxide (0.9 g) and water (20 ml) were added to a mixture of 4-ethoxycarbonylmethyl-7-fluoro-6-nitro-2H-1,4-benzoxazin-3(4H)-one (5.96 g) and 1,4-dioxane (50 ml). The mixture was stirred at room temperature for one day. Afterthe solvent was distilled off, the residue was mixed with water (100 ml), then filtered. The filtrate was acidified with hydrochloric acid, and extracted with methyl isobutyl ketone (150 ml). After the extract was washed with water, it was dried with anhydrous sodium sulfate, and then the solvent was distilled off to give the desired 4-carboxymethyl-7-fluoro-6-nitro-2H-1,4-benzoxazin-3(4H)-one (4.8 g). mp. 177°–183° C.

Example 7

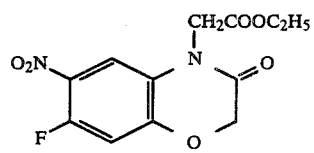

4-Ethoxycarbonylmlethyl-7-fluoro-2H-1,4-benzoxazin-3(4H)-one (20 g) was added to concentrated sulfuric acid of a temperature of 0° C. to 5° C. After the mixture was fully stirred (for about 10 minutes), 98% nitric acid (5.4 g) was added dropwise. The liquor was stirred at a temperature of 0° C. to 5° C. for 1.5 hours, and poured into ice-cold water, and then the resulting solid was recovered by filtration, and washed fully with water until washings did not exhibit any acidity, then dried. Recrystallization thereof from ethanol gave the desired 4-ethoxycarbonylmethyl-7-fluoro-6-nitro-2H-1,4-benzoxazin-3(4H)-one (21 g). mp. 79°–81° C.

Example 8

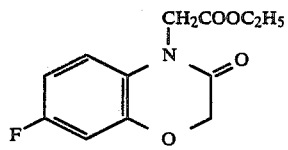

7-[4-Ethoxycarbonylmlethyl-2H-1,4-benzoxazin-3(4H)-one]diazonium tetrafluoroborate (3.49 g) was heated to a temperature of 130° C. to 135° C. for about 5 minutes until gas generation terminated. The reaction product was mixed with toluene (50 ml), and evaporated under reduced pressure to dryness. The residue was mixed with ethanol (100 ml), and treated with activated carbon. After filtration, the filtrate was distilled under reduced pressure, and the resulting residue (2.1 g)

was recrystallized from ethanol-hexane to give the desired 4-ethoxycarbonylmethyl-7-fluoro-2H-1,4-benzoxazin-3(4H)-one (0.6 g). mp. 90°–91.5° C.

Example 9

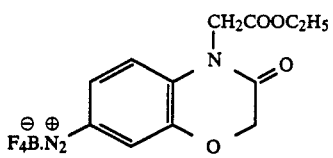

(IX)

36% Hydrochloric acid (24 g) was added to water (200 ml), and the liquor was cooled to 10° C., then 7-amino-4-ethoxycarbonylmlethyl-2H-1,4-benzoxazin-3(4H)-one (20.2 g) was added thereto and the mixture was stirred. Sodium nitrite (5.9 g) dissolved in water (30 ml) was added dropwise thereto at a temperature of 0° C. to 5° C., then 30 minutes after, 42% tetrafluoroboric acid (25 g) was added dropwise to the liquor, and it was stirred at a temperature of 0° C. to 5° C. for an hour. The desired compound was filtered off, and washed twice with 50 ml of cold water, then air-dried to give the desired 7-[4-ethoxycarbonylmethyl-2H-1,4-benzoxazin-3(4H)-one]diazonium tetrafluoroborate (22 g). mp. 129°–130° C. (decomposition).

Referential Example 1

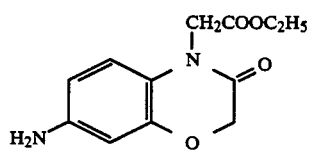

(X)

A mixture of 4-ethoxycarbonylmethyl-7-nitro-2H-1,4-benzoxazin-3(4H)-one (30 g), 10% palladium-carbon (3 g) and ethanol (150 ml) was charged in an autoclave, and catalytically reduced under conditions of 20 kg/cm² of hydrogen pressure and at a temperature of 60° C. to 70° C. Tetrahydrofuran was added thereto, and the liquor was filtered, then the filtrate was distilled under reduced pressure. Recrystallization of the resulting solid from ethanol gave the desired 7-amino-4-ethoxycarbonylmethyl-2H-1,4-benzoxazin-3(4H)-one (20 g). mp. 136°–137° C.

Referential Example 2

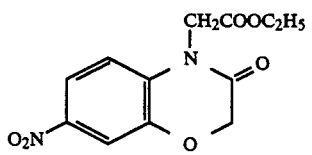

(XI)

Ethyl bromoacetate (18.4 g) was added dropwise at a temperature of 30° C. to 40° C. to a mixture of 7-nitro-2H-1,4-benzoxazin-3(4H)-one (19.4 g), potassium carbonate (15.2 g) and acetonitrile (100 ml), the mixture was refluxed under heating for 3 hours. When the reaction was completed, the liquor was filtered, the filtrate was distilled. Recrystallization of the resulting solid from toluene-hexane gave the desired 4-ethoxycarbonylmethyl-7-nitro-2H-1,4-benzoxazin-3(4H)-one (20 g). mp. 120.5°–121.5° C.

Referential Example 3

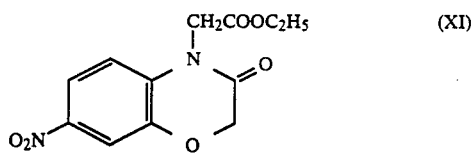

(XI)

Ethyl bromoacetate (92 g) was added dropwise at a temperature of 50° C. to 60° C. to a mixture of 2-amino-5-nitrophenol (38.5 g), potassium carbonate (106.4 g) and N,N-dimethylformamide (100 ml). After the mixture was stirred at a temperature of 100° C. to 110° C. for 6 hours, it was cooled and poured into ice-cold water (500 g). The liquor was extracted twice with toluene (300 ml), both portions of the extraction liquor were combined and washed with water, an aqueous solution of 5% potassium hydroxide, and water, in that order, and dried with anhydrous sodium sulfate, then the solvent was distilled off. Recrystallization of the residue from toluene-hexane gave the desired 4-ethoxycarbonylmethyl-7-nitro-2H-1,4-benzoxazin-3(4H)-one (30 g). When the mother liquor was distilled and recrystallized from ethanol, additional 1.3 g of the desired compound was produced. mp. 120.5°–121.5° C.

In the above Referential Example 3, the washing by the aqueous solution of 5% potassium hydroxide was acidified with concentrated hydrochloric acid, and the solvent was distilled off, then the solid was recovered by filteration, and washed with water, and then recrystallized from ethanol to give 7-nitro-2H-1,4-benzoxazin-3(4H)-one (4.1 g) of the formula (XII).

Example 10

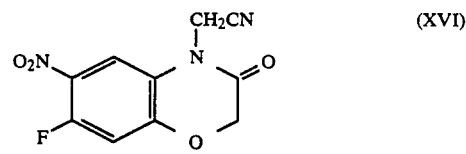

(XVI)

Two drops of N,N-dimethylformamide were added to a mixture of 4-carbamoylmethyl-7-fluoro-6-nitro-2H-1,4-benzoxazin-3(4H)-one (1.4 g), thionylchloride (1.2 g) and toluene (20 ml), and the mixture was stirred at a temperature of 100° C. to 110° C. for 6 hours. After the liquor was allowed to cool, methylisobutyl ketone (300 ml) was added thereto, and the liquor was washed with water, a saturated aqueous solution of sodium bicarbonate, water and a saturated table salt solution, in that order, subsequently dried with anhydrous sodium sulfate. After the solvent was distilled off, toluene (300 ml) and activated carbon (0.5 g) were added to the residue, the mixture was heated for a minute, and filtered while it was still hot. The resulting product was allowed to stand overnight, resulting crystals were recovered by filtration, and dried to give the desired 4-cyanomethyl-7-fluoro-6-nitro-2H-1,4-benzoxazin-3(4H)-one (0.64 g). When the residue obtained by distilling the mother liquor was recrystallized from a minimum amount of toluene, an additional amount (0.3 g) of the desired compound was produced. mp. 196°–200° C.

The product could be recognized as identical with the substance obtained from the following Example 11, by the TLC Process by using silica-gel laminates [developer: a mixed solvent consisting of tetrahydrofuran (10 ml), toluene (30 ml) and acetic acid (1 ml)].

Example 11

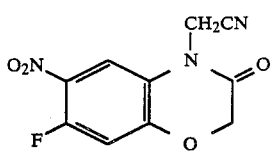
(XVI)

98% nitric acid (0.71 g) was added dropwise to acetic anhydride (11.3 ml) at a temperature of 0° C. Subsequently a few drops of concentrated sulfuric acid were added thereto as catalyst, and the mixture was stirred for a while at 0° C. 4-cyanomethyl-7-fluoro-2H-1,4-benzoxazin-3(4H)-one (2.06 g) was added little by little thereto and stirred continuously at 0° C. for 30 minutes. A solution consisting of sodium hydride (10 g) and water (88 ml), cooled previously to 0° C., was added dropwise at 0° C. to neutralize the reaction liquor. The liquor was extracted with methylisobutyl ketone, and the extraction liquor was washed with water and a table salt solution, then dried with anhydrous sodium sulfate. The solvent was distilled off to give the desired 4-cyanomethyl-7-fluoro-6-nitro-2H-1,4-benzoxazin-3(4H)-one (2.39 g). mp. 204°–206° C.

Example 12

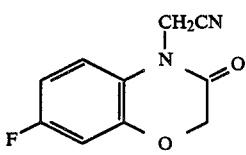
(XVII)

A mixture of 4-carbamoylmethyl-7-fluoro-2H-1,4-benzoxazin-3(4H)-one (2.24 g), toluene (20 ml), thionyl chloride (2.4 g) and N,N-dimethylformamide (3 drops) was stirred at a temperature of 90° C. to 100° C. for 2 hours. The solvent was distilled off from the mixture, and then methylisobutyl ketone (100 ml) was added thereto and the resulting mixed solution was filtered, the filtrate was washed with water, sodiumbicarbonate solution, and water, in that order, and subsequently dried with anhydrous sodium sulfate. The solvent was distilled off under reduced pressure to give the desired 4-cyanomethyl-7-fluoro-2H-1,4-benzoxazin-3(4H)-one (1.74 g). mp. 111°–113° C.

Example 13

(XV)

A mixture consisting of ethanol (15 ml), acetic acid (1 g), water (25 ml) and iron (3 g) was stirred at 80° C. 4-cyanomethyl-7-fluoro-6-nitro-2H-1,4-benzoxazin-3(4H)-one (2.51 g) was added little by little to the mixture, and stirred continuously until the gas generation terminated. The reaction liquor was filtered, and the filtrate was extracted with ethyl acetate. The residue on the other hand was extracted several times with ethyl acetate. The ethylacetate extraction liquod were put together, then washed with a solution of sodium bicarbonate and table salt, and subsequently dried with anhydrous sodium sulfate. The solvent was distilled off to give the desired 6-amino-4-cyanomlethyl-7-fluoro-2H-1,4-benzoxazin-3(4H)-one (1.77 g). mp. 163°–167° C.

Referential Example 4

[Preparation Example of the aforesaid herbicidal compound represented by the formula (E)]

N,N-dimethylformamide (3 drops) was added to a mixture consisting of 2-[4-carbamoylmethyl-7-fluoro-2H-1,4-benzoxazin-3(4H)-on-6-yl]-4,5,6,7-tetrahydro-2H-isoindole-1,3-dione (0.2 g), toluene (30 ml) and thionyl chloride (0.2 g), and then the mixture was refluxed under heating for 3 hours. After the solvent was concentrated, toluene (50 ml) was added and fully mixed therewith, and then toluene was distilled off. The resulting solid was recrystalled from ethanol to give the desired 2-[4-cyanomethyl-7-fluoro-2H-1,4-benzoxazin-3(4H)-on-6-yl]-4,5,6,7-tetrahydro-2H-isoindole-1,3-dione (0.15 g). mp. 225°–229° C.

The resulting product was recognized as identical with the compound prepared according to the below Referential Example 5, through silica-gel laminate chromatography by using, as a developing solvent, a mixed solvent of toluene-tetrahydrofuran [3 to 1 (V/V)].

Referential Example 5

[Preparation example of the aforesaid herbicidal compound represented by the formula (E)]

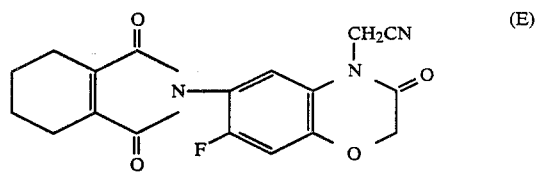
(E)

6-amino-4-cyanomethyl-7-fluoro-2H-1,4-benzoxazin-3(4H)-one (0.5 g), tetrahydrophthalic anhydride (0.38 g) and acetic acid (10 ml) were mixed with each other, then the mixture was refluxed under heating for 3 hours. After the liquor was allowed to cool, it was added to water (40 ml), and separating crystals were collected by filtration, and then the crystals were dissolved in dichloromethane (30 ml). The dichloromethane solution was washed with a saturated solution of sodium bicarbonate, and water, in that order, and then dehydrated with anhydrous sodium sulfate, and subsequently concentrated. Separated crystals were washed with a small amount of ether to give the desired 2-[4-cyanomethyl-7-fluoro-2H-1,4-benzoxazin-3(4H)-on 6-yl]-4,5,6,7-tetrahydro-2H-isoindole-1,3-dione (0.59 g). mp. 227°–229° C.

Now there is shown an embodiment of how to prepare, from the compound of the formula (IX) as a starting material, the compound of the aforesaid formula (IV) through the Processes (i), (h), (g) and (e).

Example 14

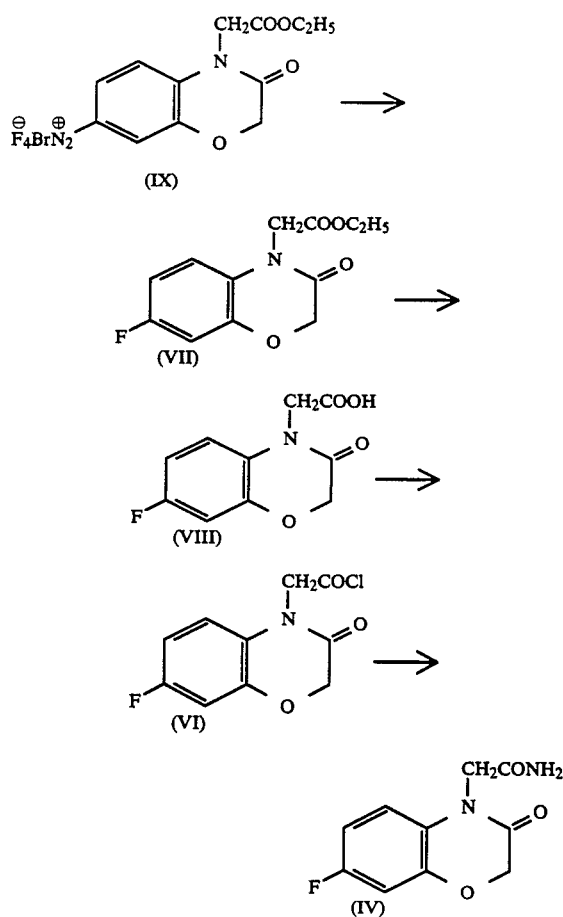

A mixture of diazonium salt (6.4 g) of the formula (IX) and xylene (160 ml) was refluxed under heating for 30 minutes. After the solvent was removed, there were added to the residue ethanol (100 ml) and an aqueous solution of sodium hydroxide (3.5 g) dissolved in water (30 ml), then the liquor was refluxed under heating for 3 hours. The reaction mixture was concentrated under reduced pressure to dryness, then the resulting residue was dissolved in water, methylisobutyl ketone (30 ml) was added thereto, and the separated aqueous layer was acidified with hydrochloric acid. The reaction mixture of hydrochloric acidity was extracted twice with methylisobutyl ketone (60 ml), the extraction liquors were dried with anhydrous sodium sulfate. The solvent was distilled off, and to the resulting residue (3.8 g) were added chloroform (51 g), thionyl chloride (6.1 g) and pyridine (6 drops), and the liquor was refluxed at a temperature of 50° C. to 60° C. for 5 hours. The solution was concentrated, toluene (50 ml) was added thereto, the mixture was filtered, the filtrate was distilled under reduced pressure to distill off remaining thionyl chloride and hydrochloric acid. Toluene (70 ml) was mixed therewith, and ammonia gas was introduced thereinto at a temperature of 10° C. to 20° C. until saturation. Then the reaction mixture was allowed to stand overnight at room temperature to filter off the solid. The solid was washed with water, a sodium bicarbonate solution, and water, in that order, then dried to give the desired compound of the formula (IV), 4-carbonylmethyl-7-fluoro-2H-1,4-benzoxazin-3(4H)-one (2.4 g). mp. 216°–219° C.

Herbicide Test Example

Pre-emergence test/weeds in upland crop fields/soil treatment

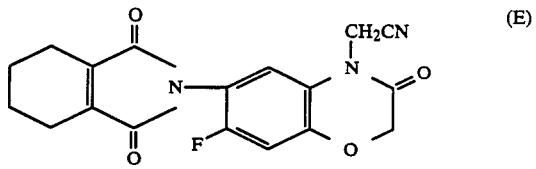

Formulation:
Carrier: 5 parts by weight of acetone
Emulsifier: 1 part by weight of benzyloxy polyglycol ether To produce a suitable preparation of active compound, 1 part by weight of active compound was mixed with the stated amount of carrier and with the stated amount of emulsifier, and the resulting emulsifiable concentrate was then diluted with water to the desired concentration.

Test Procedures:
In a greenhouse, soybean seeds were sown in 500 $cm^2$ pots filled with upland farm soil, and soil containing seeds of barnyard grass (*Echinochloa crus-galli*), pigweed (*Amaranthus lividus* L.) and goosefoot (*Chenopodium album* L.) was put over the soil in the pots in a depth of 1 cm.

One day after the sowing, a test chemical in a predetermined concentration, which was prepared in the above manner, was uniformly sprayed over the surface layer of the soil in each of the test pots.

Four weeks after the application of the active compound, the degree of damage to the weeds and the degree of phytotoxicity on the crops were determined, and recorded according to the following assessment scale.

| Rating | Herbicidal effect of active compound on weed in %* |
|---|---|
| 5 | 95% or more (fatal effect) |
| 4 | at least 80% and less than 95% |
| 3 | at least 50% and less than 80% |
| 2 | at least 30% and less than 50% |
| 1 | at least 10% and less than 30% |
| 0 | less than 10% (no effect) |
| 5 | at least 90% (fatal phytotoxicity) |
| 4 | at least 50% and less than 90% |
| 3 | at least 30% and less than 50% |
| 2 | at least 10% and less than 30% |
| 1 | more than 0% and less than 10% |
| 0 | 0% (no phytotoxicity) |

*These values (%) are those obtained by comparing the test data in the treated plant section with the test data in the control (untreated) plant section.

The test results are shown on the following table.

| Active compound | Amount of active compound (kg/ha) | Herbicidal effect on weeds | | | Phytotoxic effect on soy bean plants |
|---|---|---|---|---|---|
| | | Barnyard grass | Pigweed | Goosefoot | |
| (E) | 0.25 | 5 | 5 | 5 | 1 |
| | 0.125 | 4 | 5 | 5 | 0 |
| | 0.06 | 3 | 5 | 5 | 0 |

The novel compound of formula (I), in addition to being used as an intermediate, is itself useful was a herbicide upon formulation and use as set forth in the foregoing example.

It will be understood that the specification and Examples are illustrative but not limitative of the present invention and that other embodiments within the spirit and scope of the invention will suggest themselves to those skilled in the art.

What is claimed is:

1. 2-[4-Carbamoylmethyl-7-fluoro-2H-1,4-benzoxazin-3-(4H)-3(4H)-on-6-yl]-4,5,6,7-tetrahydro-2H-isoindole-1,3-dione of the formula (I)

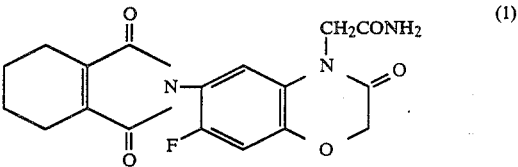

2. A herbicidal composition comprising a herbicidally effective amount of the compound according to claim 1 and a diluent.

3. A method of combating unwanted vegetation which comprises applying to such vegetation or to a locus from which it is desired to exclude such vegetation a herbicidally effective amount of the compound according to claim 1.

* * * * *

UNITED STATES PATENT AND TRADEMARK OFFICE
CERTIFICATE OF CORRECTION

PATENT NO. : 4,798,620

DATED : January 17, 1989

INVENTOR(S) : Toyohiko Kume, et al

It is certified that error appears in the above-identified patent and that said Letters Patent is hereby corrected as shown below:

| | |
|---|---|
| Title Page, under "Foreign | line 1, delete "Sep. 6, 1986" and substitute --Sep. 9, 1986--; |
| Col. 5, line 22 | Delete "4-ethoxycarbonyl" and substitute --4-ethoxycarbonylmethyl-- |
| Col. 5, line 45; Col. 10, line 65 | Correct --carbamoylmethyl-- |
| Col. 8, line 68 | Correct --dimethylaceta -- |
| Col. 12, line 38 | Correct --Ethoxycarbonylmethyl-- |
| Col. 12, line 60; Col. 13, line 16 | Correct --Ethoxycarbonylmethyl-- |
| Col. 15, line 68 | Delete "liquod" and substitute --liquor-- |
| Col. 16, line 4 | Correct --cyanomethyl-- |

Signed and Sealed this

Third Day of December, 1991

*Attest:*

HARRY F. MANBECK, JR.

*Attesting Officer*     *Commissioner of Patents and Trademarks*